United States Patent [19]

Tamaru et al.

[11] 4,310,703

[45] Jan. 12, 1982

[54] PROCESS FOR THE PREPARATION OF CYCLOHEXANONE

[75] Inventors: Akio Tamaru; Yoshio Kinsho; Takayuki Yoshida, all of Kitakyushu, Japan

[73] Assignee: Mitsubishi Chemical Industries Limited, Tokyo, Japan

[21] Appl. No.: 169,898

[22] Filed: Jul. 17, 1980

[30] Foreign Application Priority Data

Jul. 30, 1979 [JP] Japan ................................ 54-96957

[51] Int. Cl.³ ............................................ C07C 45/00
[52] U.S. Cl. ................................................ 568/361
[58] Field of Search ............... 568/403, 361; 252/407, 252/416

[56] References Cited

U.S. PATENT DOCUMENTS

| | | | |
|---|---|---|---|
| 2,633,475 | 3/1953 | Mottem | 568/403 |
| 2,746,993 | 5/1956 | Dean | 568/361 |
| 2,861,106 | 11/1958 | Opitz et al. | 568/403 |
| 3,178,373 | 4/1965 | Groebe | 252/467 |
| 3,374,184 | 3/1968 | McEvoy et al. | 252/467 |
| 3,698,859 | 10/1972 | Velten | 252/467 |
| 3,767,595 | 10/1973 | Montgemery | 252/467 |
| 3,899,446 | 8/1975 | Miya et al. | 252/467 |
| 3,935,128 | 1/1976 | Fein et al. | 252/467 |

OTHER PUBLICATIONS

Belanovich et al., Chem. Abst. vol. 92, p. 650, #22119x (1980).
Vlasenko et al., Chem. Abst., vol. 83, #66013 (1975).

Primary Examiner—Natalie Trousof
Assistant Examiner—James H. Reamer
Attorney, Agent, or Firm—Oblon, Fisher, Spivak, McClelland & Maier

[57] ABSTRACT

There is disclosed a process for preparing cyclohexanone by catalytic dehydrogenation of cyclohexanol, which comprises conducting the dehydrogenation in the presence of a copper-chromium catalyst derived from a mixture of copper oxide and chromium oxide having an atomic ratio of copper to chromium between 8:2 and 2:8, said mixture being subjected to heat treatment at a temperature of 650° to 900° C. in a non-reducing atmosphere and to subsequent reduction to provide the desired catalyst.

13 Claims, No Drawings

PROCESS FOR THE PREPARATION OF CYCLOHEXANONE

BACKGROUND OF THE INVENTION

1. Field of the Invention

This invention relates to a process for preparing cyclohexanone and more particularly to such a process by means of catalytic dehydrogenation of cyclohexanol.

2. Description of the Prior Art

One type of known catalysts for use in dehydrogenation of cyclohexanol into cyclohexanone is copper-chromium catalysts. While the catalysts of this type which are commercially available or can be prepared by hitherto known processes have a high activity and a good durability, they suffer a disadvantage in their strong tendency to cause side reactions forming by-products such as phenol, cyclohexene and the like. It is also known that the copper-chromium catalyst may be improved by addition of a certain component such as an alkali metal, an alkaline earth metal, water glass or the like ["Hanno-betsu Jitsuyo Shokubai (Practical Catalysts Classified by Reaction)", page 573, lines 2-4, Kagaku-Kogyo-Sha, Dec. 25, 1970], but such addition fails to give a satisfactory improvement.

SUMMARY OF THE INVENTION

It has been found that a copper-chromium catalyst which causes minimized side reactions and still has a high activity and a good durability, thereby eliminating or substantially reducing the disadvantage of the prior art catalysts can be obtained by heat-treating a mixture of copper oxide and chromium oxide in a specific temperature range and then reducing it, and that the use of this catalyst makes it possible to prepare cyclohexanone in high yield over an extended period of time.

Thus, it is an object of this invention to provide a process for preparing cyclohexanone which is of great advantage to commercial application.

The above object can be accomplished by a process for preparing cyclohexanone by catalytic dehydrogenation of cyclohexanol wherein the catalyst used is a copper-chromium catalyst having an atomic ratio of copper to chromium between 8:2 and 2:8, said catalyst being obtained by heat treatment of a mixture of copper oxide and chromium oxide at a temperature of 650° to 900° C. followed by reduction.

DETAILED DESCRIPTION OF THE INVENTION

The cyclohexanol which is used as the starting material according to this invention may be derived from any source. From a commercial standpoint, a product of liquid-phase oxidation of cyclohexane with oxygen, cyclohexanol isolated from this product by distillation and cyclohexanol derived from hydrogenation of phenol may be conveniently employed as the starting material.

The catalyst used in the invention is a copper-chromium catalyst obtained by heat treatment of a copper oxide-chromium oxide mixture in a specific manner and subsequent reduction thereof.

The copper oxide-chromium oxide mixture may be prepared by well-known methods for the preparation of catalysts. For this purpose, for example, the following methods can be employed.

(1) Water-soluble copper and chromium compounds such as inorganic salts (e.g., nitrates, sulfates and chlorides) or organic salts (e.g., formates, acetates and oxalates) are used to prepare an aqueous solution thereof having a predetermined atomic ratio of copper to chromium, which solution is then admixed with a precipitant such as caustic alkalis (e.g., caustic soda and potash), alkali metal carbonates (e.g., sodium carbonate and potassium carbonate), aqueous ammonia or ammonium carbonate to precipitate hydroxides of copper and chromium. The precipitate is then dried and calcined at a temperature between about 200° C. and about 500° C. in a conventional manner as employed in the preparation of catalysts.

(2) An aqueous solution of a copper salt is added to an aqueous solution of a dichromate such as sodium dichromate or ammonium dichromate to which an aqueous ammonia has been added, and the resulting precipitate is then dried and calcined as described in (1).

(3) Chromium oxide is immersed in an aqueous solution of a copper salt to deposit the salt on the chromium oxide, and is then worked up by drying and calcination as described in (1).

(4) Copper oxide is immersed in an aqueous solution of a chromium salt to deposit the salt on the copper oxide, and is then worked up by drying and calcination as described in (1).

(5) Following the procedure of method (1), copper hydroxide and chromium hydroxide are prepared separately and these hydroxides are mixed together and was dried and calcined as described in (1).

(6) A copper salt is admixed with a chromium salt and the admixture is calcined at a temperature of about 200° C. to about 500° C. in a conventional manner as employed in the preparation of catalysts.

(7) Copper oxide and chromium oxide are admixed.

In accordance with the process of this invention, the copper oxide-chromium oxide mixture as prepared by one of the above methods is first subjected to heat treatment.

The temperature at which the heat treatment is effected is approximately in the range of from 650° C. to 900° C., preferably from 700° C. to 880° C. In general, a commercially available copper oxide-chromium oxide mixture has a specific surface area of about 50 to 150 $m^2/g$. The heat treatment is preferably continued until the oxide particles have a specific surface area of 0.5 to 20 $m^2/g$, preferably 1 to 15 $m^2/g$. At the above-mentioned temperature, the duration of heat treatment is usually selected from the range of 0.5 to 30 hours, preferably 0.5 to 20 hours and more preferably 0.5 to 10 hours.

The heat treatment at an excessively low temperature brings about only poor results even if the duration of heat treatment is prolonged and at such a temperature it is difficult to obtain a catalyst which minimize side reactions. Similarly, an excessively high temperature is also unfavorable, since the final catalyst after heat treatment at such a temperature and subsequent reduction exhibits only a low activity and a poor durability.

The heat treatment is carried out in a non-reducing atmosphere, usually in an oxygen-containing gas. For example, air and inert gases such as nitrogen, argon and carbon dioxide and mixtures thereof may be used as the atmosphere and the heat treatment is preferably carried out in air.

The thus heat-treated copper oxide-chromium oxide mixture is then subjected to reduction. The reduction can be effected by any well-known means. For this purpose, gaseous reducing agents such as hydrogen and carbon monoxide and liquid reducing agents such as methanol and formalin may be used. Usually it is preferred to use hydrogen with or without an inert gas diluent such as nitrogen, argon or carbon dioxide. In such a case, the reduction is preferably continued at a temperature of 100° to 500° C., preferably 100° to 300° C., until no further exotherm resulting from the reduction is observed. Usually the reduction is performed by placing the heat-treated copper-chromium oxides into a reactor conventionally used in the dehydrogenation of cyclohexanol and passing hydrogen gas through the reactor. Following the reduction, the resulting catalyst is used for the dehydrogenation of cyclohexanol in the reactor. Since hydrogen is present in the proximity of the catalyst during the dehydrogenation, the catalyst will be conditioned to an appropriately reduced state in an early stage of dehydrogenation even if the heat-treated oxide mixture is insufficiently reduced in the above-mentioned reduction step.

The mixture of copper oxide and chromium oxide used in the present invention should have an atomic ratio of copper to chromium between 8:2 and 2:8, preferably between 7:3 and 3:7. A catalyst containing less chromium is inferior in durability, whereas a catalyst containing much chromium is also unfavorable in that it is inferior in activity and increases side reactions.

The catalyst used in the present invention may further contain one or more metals other than copper and chromium in an atomic proportion of not more than 40%, preferably 0.5 to 30% based on the sum of copper and chromium. Usually these metals are selected from, for example, sodium, potassium, calcium, barium, zinc, manganese, silicon and the like and are preferably manganese and/or barium.

The catalyst of the invention is preferably used with no carrier, although it may be supported on a suitable known carrier as required. The carriers used for this purpose include alumina, silica, diatomaceous earth, activated charcoal and the like. In the case of supported catalysts, the sum of copper and chromium should comprise at least 30%, preferably at least 40% by weight of the catalyst. If a supported catalyst contains much less copper and chromium, it cannot exert satisfactorily its effect on activity and suppression of side reactions.

The catalyst of the invention is generally used as powder or granules and usually it is preferred to use a granular catalyst. For this purpose, the catalyst may be granulated by a suitable means such as tableting, extrusion or rolling. This granulation may usually be conducted either before or after the preparation of the catalyst, but it is preferred from a commercial standpoint that the copper oxide-chromium oxide mixture be previously formed into granules prior to the heat treatment step.

The dehydrogenation of cyclohexanol according to the invention is usually performed in a vapor phase and the catalyst is used as a fixed bed or a fluidized bed. In commercial operations a fixed bed is preferably employed.

The reaction temperature is in the range of 200° to 400° C., preferably 250° to 350° C. and more preferably 250° to 300° C. If the dehydrogenation is carried out at a much lower temperature, the conversion of cyclohexanol is decreased. On the other hand, a much higher reaction temperature is unfavorable in that it causes side reactions more intensely although the conversion is still increased. The reaction pressure is not critical and a subatmospheric to superatmospheric pressure may be applied. Usually it is preferred to select a nearly atmospheric pressure.

The starting material, i.e., cyclohexanol is fed at a liquid hourly space velocity (LHSV) of from about 0.1 to about 100 hr$^{-1}$, preferably from about 0.5 to about 20 hr$^{-1}$ and it may be diluted with an inert gas such as nitrogen or steam prior to feeding to the reactor.

In accordance with the process of the present invention, cyclohexanone can be prepared in good yield over a prolonged period with little formation of by-products and the process is therefore of great advantage to commercial application.

Having generally described the invention, a more complete understanding can be obtained by reference to certain examples which are provided herein for purposes of illustration only and are not intended to be limiting in any manner.

EXAMPLES 1 TO 3 AND COMPARATIVE EXAMPLES 1 TO 4

An aqueous 28% ammonia (450 ml) was added to a solution of sodium dichromate (450 g) in demineralized water (2 l). To the resulting solution was added with stirring a solution of copper nitrate (725 g), manganese nitrate (86.1 g) and barium nitrate (26.1 g) in demineralized water (5 l) to form a precipitate, which was collected by filtration, washed with water, dried at 110° C. for 8 hours and then calcined at 300° C. for 6 hours to give an oxide mixture of copper-chromium system having an atomic ratio of copper to chromium to manganese to barium of 30:30:3:1.

The oxide mixture was then compressed into tablets and then crushed into granules having a size of about 2 mm. These granules were then heat-treated in air for 2 hours at a temperature indicated in Table 1 below, and an aliquot (10 ml) of the granules was packed into a stainless steel tubular reactor of 13 mm inner diameter. A gaseous mixture consisting of 3% hydrogen and 97% argon by volume was then passed through the reactor at a rate of 60 l/hr., while the granules were heated for 5 hours at 150° C. and for an additional 5 hours at 200° C. to effect the reduction and give the desired copper-chromium catalyst.

Subsequently, the inlet and outlet temperatures of the catalyst layer in the packed reactor were maintained at 260° C. and 280° C., respectively, and a crude cyclohexanol consisting of 80% by weight cyclohexanol, 8% cyclohexanone and 12% other components was fed at an LHSV of 2 hr$^{-1}$ after vaporization by a preheater to effect vapor-phase dehydrogenation of cyclohexanol. The reaction product was sampled at intervals and analyzed by gas chromatography.

The data of percent conversion of cyclohexanol and percent selectivity toward by-products obtained after a 30 hour reaction are shown in Table 1.

For comparison, the data obtained in cases where the heat treatment is omitted (Comparative Example 1 ) or carried out at lower temperatures (Comparative Examples 2 and 3) or at a higher temperature (Comparative Example 4) are also shown in Table 1.

TABLE 1

| | Heat treatment temp. (°C.) | % Conversion of cyclohexanol | % Selectivity toward by-products |
|---|---|---|---|
| Example 1 | 850 | 73 | 0.4 |

TABLE 1-continued

| | Heat treatment temp. (°C.) | % Conversion of cyclohexanol | % Selectivity toward by-products |
|---|---|---|---|
| 2 | 800 | 73 | 0.4 |
| 3 | 750 | 73 | 0.5 |
| Comparative Example | | | |
| 1 | No heat treatment | 73 | 3.0 |
| 2 | 450 | 73 | 2.5 |
| 3 | 600 | 73 | 1.7 |
| 4 | 950 | 15 | 0.3 |

EXAMPLE 4 AND COMPARATIVE EXAMPLE 5

An aqueous 28% ammonia (550 ml) was added to a solution of ammonium dichromate (441.4 g) in demineralized water (2 l) and to the resulting solution was added with stirring a solution of copper nitrate (845.6 g) and barium nitrate (305 g) in demineralized water (5 l) to form a precipitate, which was then collected by filtration, washed with water, dried at 110° C. for 8 hours and calcined at 300° C. for 6 hours to give an oxide mixture of copper-chromium system having an atomic ratio of copper to chromium to barium of 30:30:10.

This oxide mixture was then subjected to heat treatment at 800° C. and to subsequent reduction in the same manner as in Example 2 to give a catalyst, which was then used in the catalytic dehydrogenation of cyclohexanol as described in the foregoing examples.

As a result, the catalyst showed 73% conversion of cyclohexanol and 0.6% selectivity toward by-products.

For comparison, a catalyst prepared without the above-mentioned heat treatment was used in the same reaction. In this case, the conversion of cyclohexanol was 73% but the selectivity toward by-products was increased to 10.1%.

EXAMPLE 5 AND COMPARATIVE EXAMPLE 6

Copper nitrate (680 g) and chromium nitrate (1,130 g) were dissolved in demineralized water (8 l) and the resulting solution was warmed to 50° C. An aqueous 4 N caustic soda solution was then added at a constant rate under stirring over 30 minutes until a pH value of 9 was attained. The resulting precipitate was aged at 50° C. for 60 minutes, then collected by filtration, washed with water, dried at 110° C. for 8 hours and finally calcined at 300° C. for 8 hours to give an oxide mixture of copper and chromium having an atomic ratio of copper to chromium of 50:50.

The oxide mixture was subjected to heat treatment at 800° C. and to subsequent reduction in the same manner as in Example 2 to give a catalyst, which was then used in the dehydrogenation of cyclohexanol as described in the foregoing examples.

The results were 73% conversion of cyclohexanol and 1.0% selectivity toward by-products.

For comparison, another catalyst was prepared in a similar manner except that the heat treatment was omitted, and used in the dehydrogenation in the same way. In this case, the conversion of cyclohexanol was 73%, but the selectivity toward by-products was increased to 15.0%.

EXAMPLE 6 AND COMPARATIVE EXAMPLE 7

Following the general procedure described in Example 5 and Comparative Example 6 but using 408 g of copper nitrate and 1,582 g of chromium nitrate, an oxide mixture of copper and chromium having an atomic ratio of copper to chromium of 30:70 was obtained.

The oxide mixture was subjected to heat treatment at 800° C. and to subsequent reduction in the same manner as in Example 2 to give a catalyst, which was then used in the dehydrogenation of cyclohexanol as described in the foregoing examples.

The results were 73% conversion of cyclohexanol and 0.4% selectivity toward by-products.

For comparison, another catalyst was prepared in a similar manner except that the heat treatment step was omitted, and used in the dehydrogenation as above. In this case, the conversion of cyclohexanol was 73%, but the selectivity toward by-products was increased to 2.5%.

EXAMPLE 7 AND COMPARATIVE EXAMPLE 8

Following the general procedure described in Example 5 and Comparative Example 6 but using 952 g of copper nitrate and 678 g of chromium nitrate, an oxide mixture of copper and chromium having an atomic ratio of copper to chromium of 70:30 was obtained.

The oxide mixture was subjected to heat treatment at 850° C. and to subsequent reduction as in Example 1 to give a catalyst, which was then used in the dehydrogenation of cyclohexanol as described in the foregoing examples.

The results were 73% conversion of cyclohexanol and 0.5% selectivity toward by-products.

For comparison another catalyst was prepared in a similar manner except that the heat treatment was omitted, and used in the dehydrogenation of cyclohexanol in the same way. In this case, the conversion of cyclohexanol was 73%, but the selectivity toward by-products was increased to 19.0%.

The results of Examples 4–7 and Comparative Examples 5–8 are summarized in Table 2 below.

TABLE 2

| No. | Heat Treatment | % Conversion of cyclohexanol | % Selectivity toward by-products |
|---|---|---|---|
| Example 4 | Yes | 73 | 0.6 |
| Comparative Example 5 | No | 73 | 10.1 |
| Example 5 | Yes | 73 | 1.0 |
| Comparative Example 6 | No | 73 | 15.0 |
| Example 6 | Yes | 73 | 0.4 |
| Comparative Example 7 | No | 73 | 2.5 |
| Example 7 | Yes | 73 | 0.5 |
| Comparative Example 8 | No | 73 | 19.0 |

It can be seen from the above results that the selectivity toward by-products is significantly decreased in Examples (according to the present process) as compared to Comparative Examples while the conversion of cyclohexanol obtained in Examples is comparable to that in Comparative Examples.

In Comparative Example 4, the selectivity toward by-products was as low as 0.3%, but at the same time the conversion of cyclohexanol was extremely decreased to an impractical level (15%).

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for preparing cyclohexanone by catalytic dehydrogenation of cyclohexanol in the range of 200° to 400° C., which comprises conducting the dehydrogenation in the presence of a copper-chromium catalyst derived from a mixture of copper oxide and chromium oxide having an atomic ratio of copper to chromium between 8:2 and 2:8, said mixture being subjected to heat treatment from 0.5 to 30 hours at a temperature of 650° to 900° C. in a non-reducing atmosphere until the mixture of copper oxide and chromium oxide has a specific surface area of 0.5 to 20 m$^2$/g and to subsequent reduction to provide the desired catalyst.

2. The process of claim 1 wherein the heat treatment is carried out in an oxygen-containing gas.

3. The process of claim 1 wherein the mixture is subjected, after heat treatment, to vapor-phase reduction with a gaseous reducing agent.

4. The process of claim 3 wherein the reducing agent is hydrogen which may be diluted with an inert gas.

5. The process of claim 1 wherein the reduction is carried out at a temperature of 100° to 500° C.

6. The process of claim 1 wherein the reduction is continued at least until the exotherm resulting from the reduction ceases substantially.

7. The process of claim 1 wherein the copper-chromium catalyst further comprises, on an atomic basis, 0.5 to 30% manganese and/or barium based on the sum of copper and chromium.

8. The process of claim 1 wherein the catalyst used is formed into granules without any carrier.

9. The process of claim 1 wherein the atomic ratio of copper to chromium is between 7:3 and 3:7.

10. The process of claim 1 wherein the heat treatment is carried out at a temperature of 700° to 880° C.

11. The process of claim 1 wherein the reduction is carried out at a temperature of 100° to 300° C.

12. The process of claim 1 wherein the heat treatment is continued until the mixture of copper oxide and chromium oxide has a specific surface area of 1 to 15 m$^2$/g.

13. The process of claim 1 wherein the dehydrogenation is carried out by passing gaseous cyclohexanol through a fixed bed of the catalyst at a liquid hourly space velocity (LHSV) of 0.5 to 20 hr$^{-1}$.

* * * * *